United States Patent
Natrajan et al.

(10) Patent No.: US 8,293,908 B2
(45) Date of Patent: Oct. 23, 2012

(54) FACILE N-ALKYLATION OF ACRIDINE COMPOUNDS IN IONIC LIQUIDS

(75) Inventors: Anand Natrajan, Manchester, NH (US); David Wen, Northborough, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 258 days.

(21) Appl. No.: 12/743,622

(22) PCT Filed: Nov. 18, 2008

(86) PCT No.: PCT/US2008/083842
§ 371 (c)(1),
(2), (4) Date: May 19, 2010

(87) PCT Pub. No.: WO2009/067417
PCT Pub. Date: May 28, 2009

(65) Prior Publication Data
US 2010/0256380 A1   Oct. 7, 2010

Related U.S. Application Data

(60) Provisional application No. 60/989,242, filed on Nov. 20, 2007.

(51) Int. Cl.
*C07D 219/00* (2006.01)
(52) U.S. Cl. ...................................................... 546/102
(58) Field of Classification Search ................... 546/102
See application file for complete search history.

(56) References Cited

U.S. PATENT DOCUMENTS

| | | | |
|---|---|---|---|
| 5,438,139 A | 8/1995 | Sato et al. | |
| 5,669,819 A | 9/1997 | Mattingly et al. | |
| 6,051,719 A | 4/2000 | Benson et al. | |
| 6,171,520 B1 | 1/2001 | Imai et al. | |
| 2005/0187388 A1 | 8/2005 | Cebula et al. | |
| 2006/0154328 A1 | 7/2006 | Bruce et al. | |

OTHER PUBLICATIONS

Adamczyk et al., Journal of Organic Chemistry (1998), 63(16), 5636-5639.*

* cited by examiner

*Primary Examiner* — Nizal Chandrakumar
(74) *Attorney, Agent, or Firm* — King & Spalding LLP

(57) ABSTRACT

A method is provided for N-alkylation of acridine compounds, typically with a 1,3- propane sultone alkylating reagent, in ionic liquid solvents to provide the corresponding acridinium compounds in high yield.

20 Claims, 4 Drawing Sheets

FACILE N-ALKYLATION OF ACRIDINE COMPOUNDS IN IONIC LIQUIDS

FIELD OF INVENTION

The present invention relates generally to synthetic methods for preparing N-alkyl derivatives of heteroaromatic compounds. More particularly, the invention relates to the use of ionic liquid solvents in the N-alkylation of acridines and related compounds.

BACKGROUND OF THE INVENTION

Chemiluminescent acridinium compounds have emerged to be extremely useful labels for immunoassays and nucleic acid assays. Hydrophilic acridinium esters containing N-sulfopropyl groups (NSP) are useful for protein labeling as well as for the preparation of small molecule conjugates, as described by Law et al. in U.S. Pat. No. 5,656,426 and Natrajan et al. in U.S. Pat. No. 6,664,043, the disclosures of which are hereby incorporated by reference. These hydrophilic acridinium esters offer improved performance in immunoassays.

The synthesis of acridinium esters containing N-sulfopropyl groups entails N-alkylation of the corresponding acridine esters with the potent carcinogen 1,3-propane sultone. In general, this reaction is carried out by heating the acridine ester with a vast excess of propane sultone in the absence of solvent, as described by Law et al in U.S. Pat. No. 5,656,426, incorporated by reference herein. This reaction is illustrated in FIG. 1. The reaction as described by Law for the synthesis of NSP-DMAE-NHS ester (FIG. 1, R=NHS) suffers from several drawbacks that include a relatively low yield of isolated product (25%) and the need to use a vast excess of propane sultone (50-fold) over the acridine precursor.

As reported recently by Bolt and Golka in *Toxicology Lett.* 2004, 151, 251-254, the disclosure of which is incorporated by reference, propane sultone is directly alkylating, genotoxic and carcinogenic. Bolt and Golka observe that "malignancies observed within a group of persons exposed to 1,3-propane sultone appear surprisingly consistent with the expectations from the available animal studies" and are characterized by latency times up to 30-40 years or more after limited periods of past exposure. Thus, chemical transformations under reaction conditions that limit the use this toxic reagent are desirable.

More recently, Evangelista et al. in U.S. Pat. No. 6,924,154, the disclosure of which is hereby incorporated by reference, reported the synthesis of an acridinium ester with an N-sulfopropyl group by microwave heating of the corresponding acridine ester and a 20-fold excess of neat 1,3-propane sultone. This synthetic process required a second step to hydrolyze polysulfonated acridinium esters formed in the reaction with strong acid to convert them to the monosulfonate N-sulfopropyl group, followed by extensive chromatographic purification to afford an overall yield of 53% of the N-sulfopropyl-containing acridinium ester. Clearly, if the acridine ester contains acid-sensitive functional groups, such as the NHS ester, the acid hydrolysis step cannot be performed and the overall yield of the desired monosulfonate product is likely to be quite low, as observed by Law in U.S. Pat. No. 5,656,426. Moreover, the necessity for extensive chromatographic purification of the product is also undesirable.

Adamczyk et al. in *J. Org. Chem.* 1998, 63, 5636-5639, the disclosure of which is hereby incorporated by reference, reported that the introduction of the N-sulfopropyl group in acridine sulfonamides can be performed using the reagent neopentyl 3-trifloxypropane sulfonate. Although this procedure obviates using 1,3-propane sultone, the reagent 3-trifloxypropane sulfonate had to be synthesized separately and moreover, N-alkylation using this reagent required 7 days to afford 34% conversion to product.

The above cited literature points to the general difficulty in introducing the N-sulfopropyl group in acridine compounds which necessitates conducting the reaction in neat alkylating reagent, such as propane sultone, at elevated temperatures followed by acid treatment to hydrolyze polysulfonated material and subsequent extensive chromatographic purification of the desired N-sulfopropyl acridinium ester. Clearly, a suitable and relatively benign reaction medium that would be conducive to achieving this chemical transformation in good yields but using only limited quantities of propane sultone and without the need for extensive chromatographic purification would be beneficial. Moreover, any process that minimizes polysulfonate formation, would permit the N-alkylation of acridine esters containing acid sensitive functional groups.

In recent years, ionic liquids (ILs) have becoming increasingly popular for conducting chemical reactions and are commonly referred to as "green solvents" not only because they can be recycled but, also because of their extremely low volatility, low toxicity, non-flammability, high thermal stability and, their ability to dissolve a wide range of solutes. A review by Holbrey and Seddon in *Clean Products and Processes* 1999, 1, 223-236, the disclosure of which is hereby incorporated by reference, describes some of the properties of ionic liquids. Another review by Hagiwara and Ito in *J. Fluorine Chem.* 2000, 105, 221-227, incorporated by reference herein, describes room temperature ionic liquids of alkylimidazolium cations and fluoroanions. Hagiwara and Ito state that "a room temperature ionic liquid, or molten salt, is defined as a material containing only ionic species without any neutral molecules and having a melting point of less than 298 K." Many ionic liquids derived from alkylimidazolium cations are commercially available and two in particular that have been used in the literature are 1-butyl-3-methylimidazolium hexafluorophosphate [BMIM][PF6] and 1-butyl-3-methylimidazolium tetrafluoroborate [BMIM][BF4].

Ionic liquids have been explored as reaction media for various synthetic organic transformations including oxidations as described by Earle et al. in *Org. Lett.* 2004, 6, 707-710; Heck reaction as described by Mo et al. in *J. Am. Chem. Soc.* 2005, 127, 751-760; N-alkylation of pyrroles and indoles as described by Jorapur et al. in *Tetrahedron Lett.* 2006, 47, 2435-2438; N-alkylation of phthalimides as described by Le et al. in *Synthesis* 2004, 2, 208-212; and peptide synthesis as described by Miao and Chan in *J. Org. Chem.* 2005, 70, 3251-3255, the disclosures of which are hereby incorporated by reference. U.S. Patent Pub. 2007/0142690 to Elomari, the disclosure of which is hereby incorporated by reference, discloses alkylation of olefins with isoparaffins in ionic liquids. The use of ILs as reaction media for the N-alkylation of acridine esters to N-sulfopropyl acridinium esters has not been reported in the literature.

While ionic liquids have found utility in a variety of synthetic transformations, their use to date has been rather limited, particularly with regard to commercial scale syntheses.

SUMMARY OF THE INVENTION

It has surprisingly been discovered that acridine compounds are efficiently converted to acridinium compounds by contacting said acridine compounds with an alkylating reagent in an ionic liquid solvent. By this method, the amount of alkylating reagent is greatly reduced as compared to prior methods, which is particularly advantageous where the alkylating reagents are highly toxic and/or carcinogenic.

In accordance with a first aspect of the invention, a method is provided for N-alkylation of an acridine compound, the method comprising providing a reaction mixture comprising the acridine compound, an alkylating agent, and an ionic liquid solvent, and heating the reaction mixture to between about 100° C. and about 200° C., to thereby convert the acridine compound to an N-alkyl acridinium compound. There is essentially no constraint on the structure of the acridine compound, which may comprise acridine ester or sulfonamides, both formed at the C-9 position of the acridinium nucleus. In various non-limiting embodiments, the molar ratio of the alkylating agent to the acridine compound is less than about 20:1, typically less than about 15:1, and preferably less than about 10:1, and the ionic liquid solvent is present in a molar ratio to the acridine compound of at least about 1:1, more typically at least about 2:1, and preferably at least about 5:1.

The overall percent conversion from acridine to acridinium which may be achieved by the methods of the invention exceed those of known methods, and will typically be greater than about 70%, more typically greater than about 75%, preferably greater than about 80%, and ideally will be greater than about 85%. The high efficiency of conversion is due in part to the minimization of polyalkylation in the ionic liquid solvents, which represents a surprising and useful advance over known methods.

The preferred ionic liquid solvents according to the foregoing method have the form:

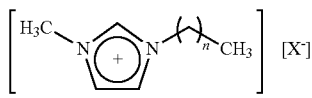

where n is an integer from one to nine, preferably from 1 to 5, and more preferably n=3; and X represents an anion which may be a member of the group consisting of: tetrachloroaluminate; hexafluoroantimonate; dicyanamide; thiocyanate; nitrate; halide; trifluoroacetate; tetrafluoroborate; hexafluorophosphate; methylsulfonate; trifluoromethylsulfonate; tris(pentafluoroethyl)trifluorophosphate; bis(trifluoromethylsulfonyl)imide; or a combination thereof. Preferably, X is tetrafluoroborate or hexafluorophosphate.

In various embodiments, the ionic solvent comprises [BMIM][PF$_6$] (1-butyl-3-methylimidazolium hexafluorophosphate) or [BMIM][BF$_4$] (1-butyl-3-methylimidazolium tetrafluoroborate), each being a preferred ionic liquid solvent in the practice of the invention for use alone or in combination.

The alkylating agent is not particularly restricted and can be selected, for example, from the group consisting of: sultones; esters of haloacetic acid; and alkyl halides or alkyl triflates, wherein the alkyl groups optionally comprise one or more heteroatoms and unsaturated bonds; with sultones being the preferred alkylating reagents, in particular those having the structure:

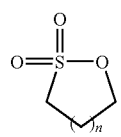

where n=1 or 2, which by name are 1,3-propane sultone and 1,4-butane sultone, respectively, 1,3-propane sultone being the most preferred alkylating reagent according to the present invention.

In another aspect of the invention, the foregoing method has been found especially useful for preparing acridinium ester compounds having the structure of formula (V):

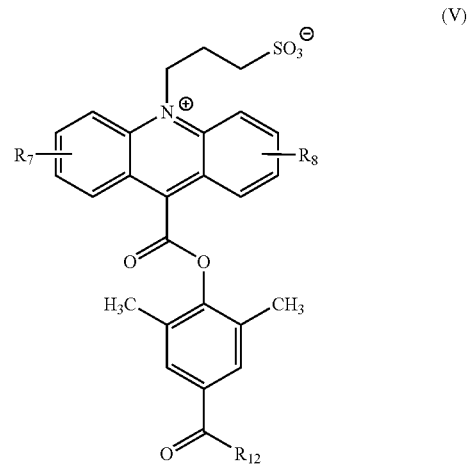

(V)

wherein $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; and wherein $R_{12}$ is selected from the group consisting of:
(i) —OR;
(ii) —O—N-succinimidyl;
(iii) —NH—(CH$_2$)$_5$—C(=O)—O—N-succinimidyl; and
(iv) —NH—(C$_2$H$_4$O)$_n$—C$_2$H$_4$NH—C(=O)—(CH$_2$)$_3$—C(=O)—O—N-succinimidyl, wherein n=0 to 5.

The method according to this aspect comprises: (1) providing a reaction mixture comprising an acridine compound, 1,3-propane sultone, and an ionic liquid solvent, the acridine compound having the structure of formula (Vb):

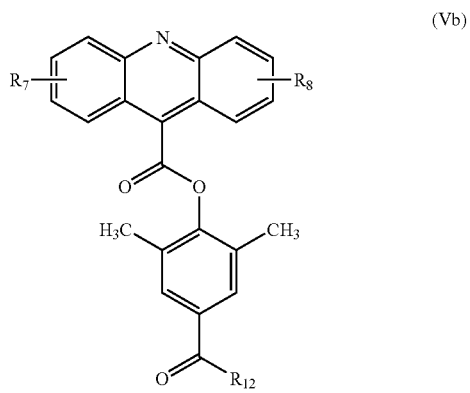

(Vb)

wherein $R_7$, $R_8$, and $R_{12}$ are as defined above; and
(2) heating said reaction mixture to between about 100° C. and about 200° C., to thereby convert said acridine compound of formula (Vb) to said acridinium ester compound of formula (V). While any molar ratio of 1,3-propane sultone to acridine compound is contemplated to be useful, in various non-limiting embodiments, the molar ratio of 1,3-propane sultone to the acridine compound will be less than about 20:1, typically less than about 15:1, and preferably less than about 10:1. Similarly, any amount of ionic liquid solvent may be employed, however, the ionic liquid solvent is usually present in a molar ratio to the acridine compound of at least about 1:1, more typically at least about 2:1, and preferably, at least about 5:1.

In a further aspect, a method is provided for preparing an acridinium sulfonamide compound having the structure of formula (VI):

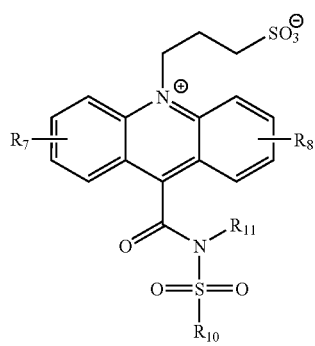

wherein $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; and wherein $R_{10}$ and $R_{11}$ can be the same or different and represent alkyl, alkenyl, alkynyl, aryl, or aralkyl groups containing up to 20 heteroatoms; the method comprising:

(1) providing a reaction mixture comprising an acridine compound, 1,3-propane sultone, and an ionic liquid solvent, the acridine compound having the structure of formula (VIa):

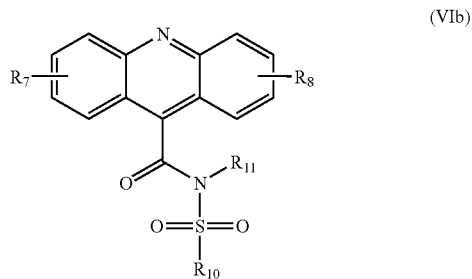

wherein $R_7$, $R_8$, $R_{10}$ and $R_{11}$ are as defined above; and (2) heating the reaction mixture to between about 100° C. and about 200° C., to thereby convert the acridine compound of formula (VIb) to the acridinium sulfonamide compound of formula (VI). The relative amounts of 1,3-propane sultone, acridine, and ionic solvent are not particularly limited, and may be as specified above.

These and other aspects of the invention will be better understood by reference to the following detailed description, accompanying figures, and appended claims.

DETAILED DESCRIPTION

Figure 1:
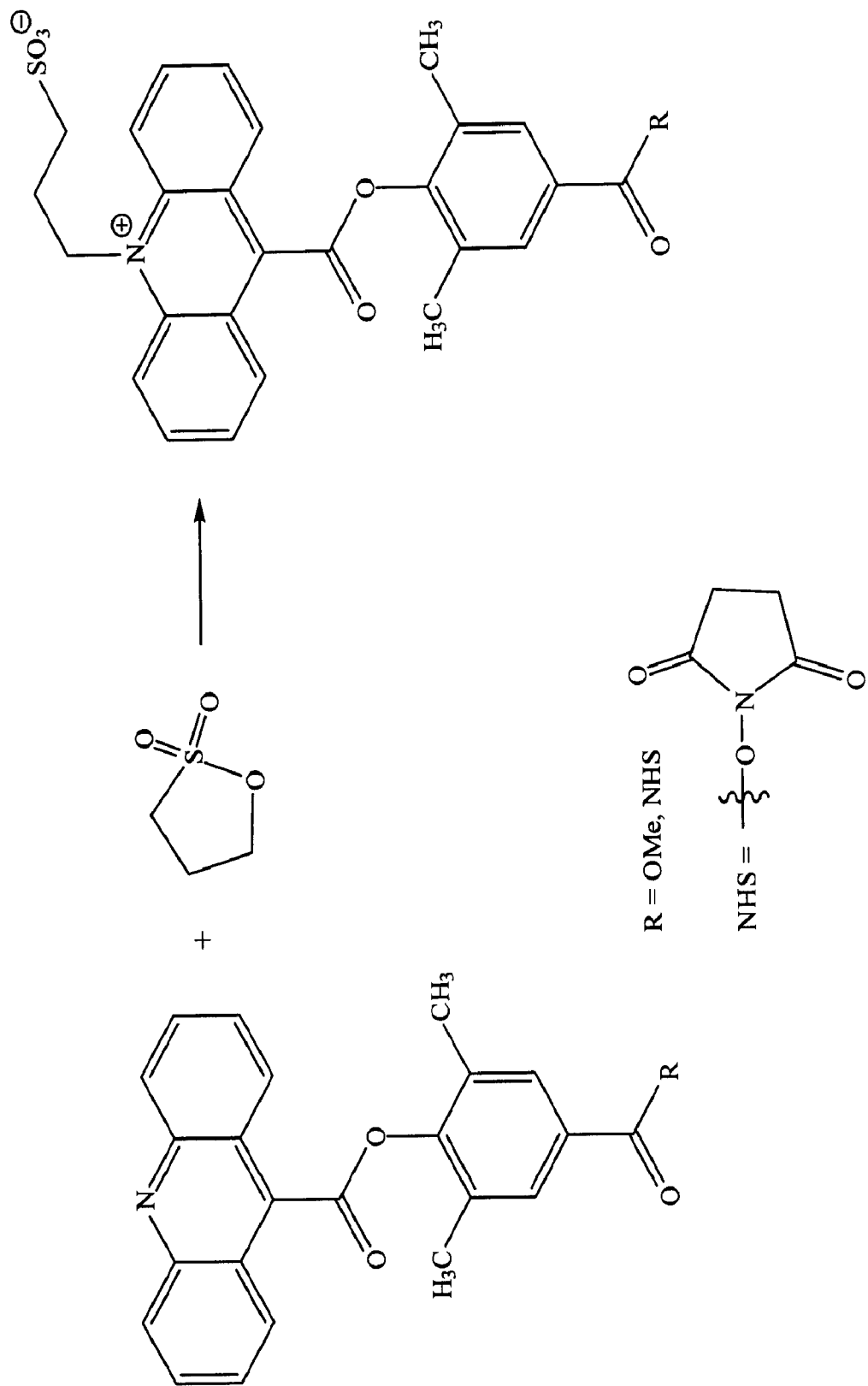
FIG. 1 illustrates the N-alkylation of an acridine ester with the potent carcinogen 1,3-propane sultone in the absence of solvent for the synthesis of NSP-DMAE-NHS(R=NHS), as described by Law et al in U.S. Pat. No. 5,656,426, and for the synthesis of NSP-DMAE-OMe (R=OMe)

All terms used herein are intended to have their ordinary meaning in the art unless otherwise specified. The term "ionic liquid" refers to a room temperature or near room temperature (e.g., ±20° C.) ionic liquid (or molten salt) which is a material containing only ionic species without any neutral molecules and having a melting point of less than 298 K. By the phrase "without any neutral molecules" is meant that the ionic liquid consists of a cationic and anionic component at its most fundamental level, but is not intended to mean that the solvent system which comprises the ionic liquid solvent does not comprise neutral species in addition to the ionic liquid.

The present invention is directed generally to a process for the synthesis of acridinium compounds, in particular acridinium esters and acridnium sulfonamides, by the N-alkylation of the corresponding acridine compounds in ionic liquids (ILs). The process is particularly useful for the preparation of hydrophilic acridinium esters and sulfonamides. The inventive transformation may be illustrated generally as follows:

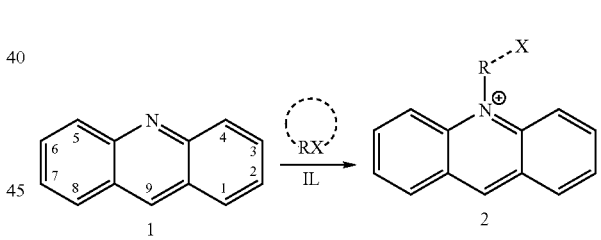

wherein acridine compound 1 is converted to acridinium compound 2 by treatment with an alkyating reagent RX in an ionic liquid solvent. The alkylating reagent RX comprises an alkyl portion R and a leaving group X. As indicated by the dashed lines, R may be a divalent radical which together with X forms a ring, such that X may be advantageously included in the acridinum compound 2 to impart functionality (e.g., increased hydrophilicity or as a starting point for further transformations). While this scheme illustrates the simple case of an unsubstituted acridine compound, the advantages of the invention may be most fully realized where the acridine compound bears addition functional groups, such as ester or sulfonamide groups at the C-9 position and/or electron donating groups at the C2 and/or C7 positions of the acridine nucleus which are more difficult to alkylate.

Advantages of the inventive process include improved chemical conversion and isolated yields of product, reduction in the formation of byproducts, such as polysulfonated byproducts which conventionally result from the use of alkyl sultone alkylating reagents, and reduction in the use highly toxic alkylating agents, such as the potent carcinogen 1,3-propane sultone. The present process also offers a general procedure for the high yield synthesis of hydrophilic acridinium esters containing N-sulfoalkyl groups, such N-sulfopropyl groups, on a gram scale. The present invention is also contemplated to be useful in general for the N-alkylation of acridine compounds with other alkylating agents.

The reaction mixture will comprise an ionic liquid which is liquid at or near room temperature. Ionic liquids typically comprise an organic cation and an anion, the anion sometimes but not always, being a purely inorganic species. The organic cation is typically a quaternary ammonium compound, including tetra-alkyl ammonium, and more typically is an N-alkyl heteroaromatic species, for example N-alkylpyridinium, 1,3-dialkylimidazolium, N-dialkylpyrrolidinium, or the like. In addition, phosphonium and sulphonium-based ionic liquids may also be suitable, although these are less preferred cations according to the invention.

Of the various N-alkyl heteroaromatic cations, special mention may be made of N-alkylpyridinium and 1,3-dialkylimidazolium cations. N-alkylpyridinium cations may generally be represented by formula (I):

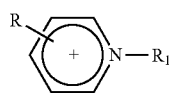

(I)

where $R_1$ is a $C_{1-20}$ hydrocarbon radical, such as alkyl, alkenyl, alkynyl, aryl, and aralkyl (e.g., benzyl), each optionally including one or more heteroatoms selected from halogen, oxygen, sulfur, and combinations thereof, with the proviso that the heteroatoms do not form moieties reactive with the alkylating reagent or with the acridine compound; and where R is intended to represent optional substitution at one or more carbon atoms of the ring, and will typically be selected from hydrogen, halogen, or alkyl (methyl, ethyl, propyl, butyl, pentyl, hexyl, etc.), and which also may comprise one or more heteroatoms, subject to the same proviso as above. Often $R_1$ will be a $C_{1-20}$ alkyl group, more typically a $C_{1-10}$ alkyl group, preferably a $C_{1-6}$ alkyl group, with methyl, ethyl, propyl, isopropyl, n-butyl, isobutyl, n-pentyl, neopentyl, and isopentyl being illustrative. R represents a substituent at any carbon atom and is usually hydrogen, but may also be methyl, ethyl, propyl, and the like. Representative of the various N-alkylpyridinium cations of formula (I) are N-methylpyridinium, N-ethylpyridinium, N-propylpyridinium, N-butylpyridinium, N-pentylpyridinium, and N-hexylpyridinium, without limitation.

In a preferred embodiment, the ionic liquid will comprise a 1,3-dialkylimidazolium cation. Such cations will typically have the structure shown in formula (II):

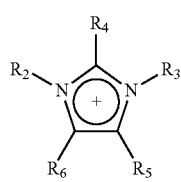

(II)

where $R_2$ and $R_3$ independently represent $C_{1-20}$ hydrocarbon radicals, such as alkyl, alkenyl, alkynyl, aryl, and aralkyl (e.g., benzyl), each optionally including one or more heteroatoms selected from halogen, oxygen, sulfur, and combinations thereof, with the proviso that the heteroatoms do not form moieties reactive with the alkylating reagent or with the acridine compound; and $R_4$, $R_5$, and $R_6$ are independently selected from hydrogen, halo, alkyl, (methyl, ethyl, propyl, butyl, pentyl, hexyl, etc.), and which also may comprise one or more heteroatoms, subject to the same proviso as above. In preferred embodiments, $R_2$ and $R_3$ will independently be $C_{1-20}$ alkyl groups, more typically $C_{1-10}$ alkyl groups, preferably $C_{1-6}$ alkyl groups, with methyl, ethyl, propyl, isopropyl, n-butyl, isobutyl, n-pentyl, neopentyl, and isopentyl being illustrative. Radicals which include one or more heteroatoms, not reactive under the conditions of the invention, may be exemplified by, for example, alkyl groups having oxa (i.e., ethers) substitution, and fluoroalkyl or perfluoroalkyl substituents.

Representative 1,3-dialkylimidazolium cations of formula (II) include, but are not limited to, those given in Table 1.

TABLE 1

Exemplary 1,3-dialkylimidazolium cations of formula (II)

| $R_2$ | $R_3$ | $R_4$ | $R_5$ | $R_6$ |
|---|---|---|---|---|
| $CH_3$ | $CH_3$ | H | H | H |
| $CH_3$ | $CH_3CH_2$ | H | H | H |
| $CH_3$ | $CH_3CH_2$ | $CH_3$ | H | H |
| $CH_3$ | $CH_3CH_2$ | H | $CH_3$ | H |
| $CH_3$ | $CH_3CH_2$ | H | H | $CH_3$ |
| $CH_3$ | $CF_3CH_2$ | H | H | H |
| $CH_3$ | $CH_3CH_2CH_2$ | H | H | H |
| $CH_3$ | $CH_3CH_2CH_2$ | $CH_3$ | H | H |
| $CH_3$ | $CH_3CH_2CH_2$ | H | $CH_3$ | H |
| $CH_3$ | $CH_3CH_2CH_2$ | H | H | $CH_3$ |
| $CH_3$ | $CH_3OCH_2CH_2$ | H | H | H |
| $CH_3$ | $CH_3CH_2CH_2CH_2$ | H | H | H |
| $CH_3$ | $CH_3CH_2CH_2CH_2$ | $CH_3$ | H | H |
| $CH_3$ | $CH_3CH_2CH_2CH_2$ | H | $CH_3$ | H |
| $CH_3$ | $CH_3CH_2CH_2CH_2$ | H | H | $CH_3$ |
| $CH_3$ | $(CH_3)_2CH_2CH_2$ | H | H | H |
| $CH_3$ | $CH_3CH_2CH_2CH_2CH_2$ | H | H | H |
| $CH_3$ | $CH_3CH_2CH_2CH_2CH_2CH_2$ | H | H | H |
| $CH_3$ | $(C_6H_5)CH_2$ | H | H | H |
| $CH_3CH_2$ | $CH_3CH_2$ | H | H | H |
| $CH_3CH_2$ | $CH_3CH_2$ | $CH_3$ | H | H |
| $CH_3CH_2$ | $CH_3CH_2CH_2$ | H | H | H |
| $CH_3CH_2$ | $CH_3CH_2CH_2CH_2$ | H | H | H |
| $(C_6H_5)CH_2$ | $CH_3CH_2CH_2$ | $CH_3$ | H | H |
| $(C_6H_5)CH_2$ | $CH_3CH_2CH_2CH_2$ | $CH_3$ | H | H |
| $(C_6H_5)CH_2$ | $(CH_3CH_2)(CH_3)CH$ | $CH_3$ | H | H |
| $(C_6H_5)CH_2$ | $CH_3CH_2CH_2CH_2$ | $CH_3$ | H | H |

Special mention may be made of 1-ethyl-3-methyl imidazolium, 1-propyl-3-methyl imidazolium, 1-butyl-3-methyl imidazolium, 1-pentyl-3-methyl imidazolium, 1-hexyl-3-methyl imidazolium, 1-heptyl-3-methyl imidazolium cation, and 1-octyl-3-methyl imidazolium. The 1-butyl-3-methyl imidazolium, which is frequently designated [BMIM] in the literature, is the currently preferred cation in the ionic liquids useful in the practice of the invention.

Other cations contemplated to be suitable include, without limitation, pyrrolidinium cations, such as 1-butyl-1-methylpyrrolidinium, alkyl ammonium cations, including tri(ethyl)hexylammonium and ethyl dimethyl propyl ammonium, and phosphonium cations, for example, tri(hexyl)tetradecylphosphonium.

A wide variety of anions, which may be inorganic or organic species, may be employed as the counterion in the ionic liquid, including without limitation metal or metalloid halide anions, such as tetrachloroaluminate ($AlCl_4^-$), tetrabromoaluminate ($AlBr_4^-$), hexafluoroantimonate ($SbF_6^-$), hexafluoroarsenate ($AsF_6^-$), to name a few. Other suitable anions include, without limitation, halide ions (Cl$^-$, Br$^-$, and I$^-$), perchlorate, hydroxide, F(HF)$_n{}^-$, tetrafluoroborate (BF$_4{}^-$), tetrachloroborate, hexafluorophosphate (PF$_6{}^-$), nitrate, trifluoromethane sulfonate (triflate), methylsulfonate (mesylate), p-toluenesulfonate (tosylate), dicyanamide, perfluorobutyl sulfonate, trifluoroacetate (CF$_3$COO$^-$), CF$_3$CF$_2$CF$_2$COO$^-$, dibutyl phosphate, carbonate, lactate, tris(pentafluoroethyl)trifluorophosphate [(C$_2$F$_5$)$_3$PF$_3$]$^-$, bis(trifluoromethylsulfonyl)imide [(CF$_3$SO$_2$)$_2$N$^-$], bis(perfluoroethylsulfonyl)imide, hydrogen sulfate, methyl carbonate, C$_{1-16}$alkyl sulfate, including for example, methyl sulfate, ethyl sulfate, and octyl sulfate, 2-(2-methoxyethoxy)ethyl sulfate, thiocyanate, tris(trifluoromethylsulfonyl)methide [(CF$_3$SO$_2$)$_3$C$^-$], and the like.

In one embodiment, the anion is a fluorine-containing anion. In another embodiment, the anion is an inorganic fluorine-containing ion. Preferably, the anion is tetrafluoroborate (BF$_4{}^-$) or hexafluorophosphate (PF$_6{}^-$). While any ionic liquid which is molten at room temperature is contemplated to be useful according to the invention, the preferred ionic liquids will be tetrafluoroborate (BF$_4{}^-$) or hexafluorophosphate (PF$_6{}^-$) salts of the cations according to formulas (I) and (II).

The most preferred ionic liquids according to the invention, may be described generally by formula (III):

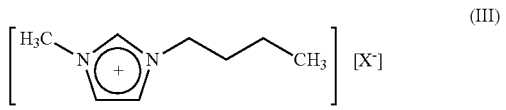

(III)

which is abbreviated herein as [BMIM][X$^-$], where X$^-$ represents any of the anions listed herein, with preference given to tetrafluoroborate [BF$_4{}^-$] and hexafluorophosphate [PF$_6{}^-$] in view of the excellent results obtained with these compounds. The ionic liquids of these two anions are thus designated [BMIM][BF$_4{}^-$] and [BMIM][PF$_6{}^-$], respectively. Exemplary ionic liquids according to formula (III) include, without limitation:

1-butyl-3-methylimidazolium tetrachloroaluminate;
1-butyl-3-methylimidazolium hexafluoroantimonate;
1-butyl-3-methylimidazolium dicyanamide;
1-butyl-3-methylimidazolium thiocyanate;
1-butyl-3-methylimidazolium nitrate;
1-butyl-3-methylimidazolium chloride;
1-butyl-3-methylimidazolium iodide;
1-butyl-3-methylimidazolium trifluoroacetate;
1-butyl-3-methylimidazolium tetrafluoroborate;
1-butyl-3-methylimidazolium hexafluorophosphate;
1-butyl-3-methylimidazolium methylsulfonate;
1-butyl-3-methylimidazolium trifluoromethylsulfonate;
1-butyl-3-methylimidazolium tris(pentafluoroethyl)trifluorophosphate;
1-butyl-3-methylimidazolium bis(trifluoromethylsulfonyl)imide.

Other non-limiting examples of ionic liquids contemplated to be useful in the practice of the synthetic methods described herein are those wherein the butyl group of the foregoing ionic liquids is replaced with other C$_{1-10}$ alkyl chains, such as methyl, ethyl, propyl, pentyl, hexyl, heptyl, octyl, nonyl, or decyl. Additional non-limiting examples of ionic liquids are those other than formula (III) ionic liquids, such as:

tri(ethyl)hexylammonium tetrafluoroborate;
tri(ethyl)hexylammonium hexafluorophosphate;
tri(ethyl)hexylammonium hexafluoroantimonate;
tri(ethyl)hexylammonium bis(trifluoromethylsulfonyl)imide;
tri(hexyl)tetradecylphosphonium tetrafluoroborate;
tri(hexyl)tetradecylphosphonium hexafluorophosphate;
tri(hexyl)tetradecylphosphonium hexafluoroantimonate;
tri(hexyl)tetradecylphosphonium bis(trifluoromethylsulfonyl)imide;
1-butyl-1-methylpyrrolidinium tetrachloroaluminate;
1-butyl-1-methylpyrrolidinium hexafluoroantimonate;
1-butyl-1-methylpyrrolidinium tetrafluoroborate;
1-butyl-1-methylpyrrolidinium hexafluorophosphate;
1-butyl-1-methylpyrrolidinium methylsulfonate;
1-butyl-1-methylpyrrolidinium trifluoromethylsulfonate;
1-butyl-1-methylpyrrolidinium tris(pentafluoroethyl)trifluorophosphate;
1-butyl-1-methylpyrrolidinium bis(trifluoromethylsulfonyl)imide;
N-butylpyridinium tetrachloroaluminate;
N-butylpyridinium hexafluoroantimonate;
N-butylpyridinium tetrafluoroborate;
N-butylpyridinium dicyanamide;
N-butylpyridinium thiocyante;
N-butylpyridinium nitrate;
N-butylpyridinium chloride;
N-butylpyridinium idoide;
N-butylpyridinium hexafluorophosphate;
N-butylpyridinium trifluoroacetate;
N-butylpyridinium methylsulfonate;
N-butylpyridinium trifluoromethylsulfonate;
N-butylpyridinium tris(pentafluoroethyl)trifluorophosphate;
N-butylpyridinium bis(trifluoromethylsulfonyl)imide; and
ethyl dimethyl propyl ammonium bis(trifluoromethylsulfonyl)imide.
ethyl dimethyl propyl ammonium hexafluorophosphate;
ethyl dimethyl propyl ammonium tetrafluoroborate; and
ethyl dimethyl propyl ammonium hexafluoroantimonate.

The ionic liquids are preferably of high purity, by which is meant greater than 95% purity, more preferably greater than 97% purity, and more preferred still greater than 98% purity, and optimally will be greater than 99% pure. Reference to purity herein will be understood to mean the absence of unreacted starting materials and byproducts from the reactions typically employed to form the ionic liquids, but does not necessarily preclude the presence of co-solvents, for example acetonitrile, to modify the viscosity and ionic conductivity of the solvent system, although in practice the use of co-solvents is not preferred.

The alkylating agent may be any organic moiety comprising a leaving group, but will typically be selected from sultones; esters of haloacetic acid (e.g., methyl bromoacetate); and compounds of the formula RL where R is any suitable C$_{1-20}$ hydrocarbon radical, optionally substituted with one or more heteroatoms and optionally including unsaturated bonds, and L is any leaving group, such as halogen (preferably iodo) or triflate. The sultones will have the general structure:

(IV)

where n is an integer typically from 1 to 4, more typically from 1 to 3, and preferably is 1 or 2. Where n=1 the sultone is 1,3-propane sultone and where n=2 the sultone is 1,4-butane sultone. 1,3-propane sultone represents the preferred alkylating reagent according to the invention, due in part to the desirability of acridinium esters functionalized with N-sulfopropyl groups in chemiluminescent immunoassays and the like. Accordingly, the following discussion of the development of the inventive method is described in relation to 1,3-propane sultone but will be understood to be generally extensible to all suitable alkylating reagents.

The present invention resulted from extensive efforts to identify a reaction medium conducive for carrying out the N-alkylation of acridine compounds with alkylating reagents such as 1,3-propane sultone where chemical conversion to the N-alkylated product is at least 70% and preferably >80%. It was also desired to achieve this chemical transformation using only limited quantities of the alkylating reagent, preferably no more than a 10-fold excess over the acridine compound, due to the extreme toxicity of 1,3-propane sultone, which has heretofore been employed in large excess in the reaction, usually in the absence of solvent. It was further desired to achieve the N-alkylation reaction using 1,3-propane sultone under reaction conditions that minimize polysulfonate formation so that acid hydrolysis of polysulfonated material formed in the reaction is not always required. However, no method for accomplishing these goals was known or readily apparent.

In our initial efforts, we investigated the N-alkylation of the acridine methyl ester illustrated in FIG. 1 with a 10-fold excess of distilled 1,3-propane sultone in various solvents at elevated temperatures to ensure efficient conversion. These small scale reactions were conducted as described in Example 1 and the extent of product formation was estimated by HPLC analysis (High Pressure Liquid Chromatography) of the crude reaction mixtures. The solvents that were investigated ranged from non-polar xylene to polar aprotic solvents such as dimethyl formamide (DMF), dimethyl sulfoxide (DMSO), diethylene glycol diethyl ether (DGDE), sulfolane and the ionic liquids 1-butyl-3-methylimidazolium tetrafluoroborate [BMIM][BF4] and hexafluorophosphate [BMIM][PF6]. The effect of added bases such as 2,6-di-t-butylpyridine and 2,6-di-t-butyl-4-methylpyridine in sulfolane on the extent of product formation were also investigated. The results of these measurements are summarized in Table 2.

TABLE 2

N-Alkylation of Acridine Methyl Ester with Propane Sultone

| Solvent | T (° C.) | hours | Base; (eq.) | % conversion |
|---|---|---|---|---|
| xylene | 140 | 4 | — | 5 |
| DMSO | 155 | 1 | — | <10 |
| DMSO | 155 | 16 | — | 0 |
| DGDE | 155 | — | — | 0 |
| DMF | 155 | 6 | — | 40 |
| sulfolane | 155 | 6 | — | 60 |
| sulfolane | 155 | 24 | — | 67 |
| sulfolane | 210 | 2 | — | 55 |
| sulfolane | 155 | 3 | DtBP; (5) | 60 |
| sulfolane | 155 | 4 | DtBMP; (5) | 60 |
| [BMIM] [BF$_4$] | 155 | 16 | — | 82 |
| [BMIM][PF$_6$] | 155 | 24 | — | 87 |

The solvent xylene led to poor conversion and in DMSO, product formation was minimal at short reaction times of one hour with substantial decomposition observed at a longer reaction time of 16 hours. The reaction in DMF was marginally better with 40% conversion while hardly any reaction was observed in DGDE. The solvent sulfolane afforded modest conversion to product of 60% after 6 hours which showed only marginal improvement to 67% after 24 hours at 155° C. Increasing the temperature of the reaction in sulfolane to 210° C. did not improve conversion to product which was observed to be 55%. Also, the inclusion of the bases 2,6-di-t-butylpyridine (DtBP) or 2,6-di-t-butyl-4-methylpyridine (DtBMP) in the reactions in sulfolane did not improve the extent of product formation which was 60% in both cases.

Figure 2A:
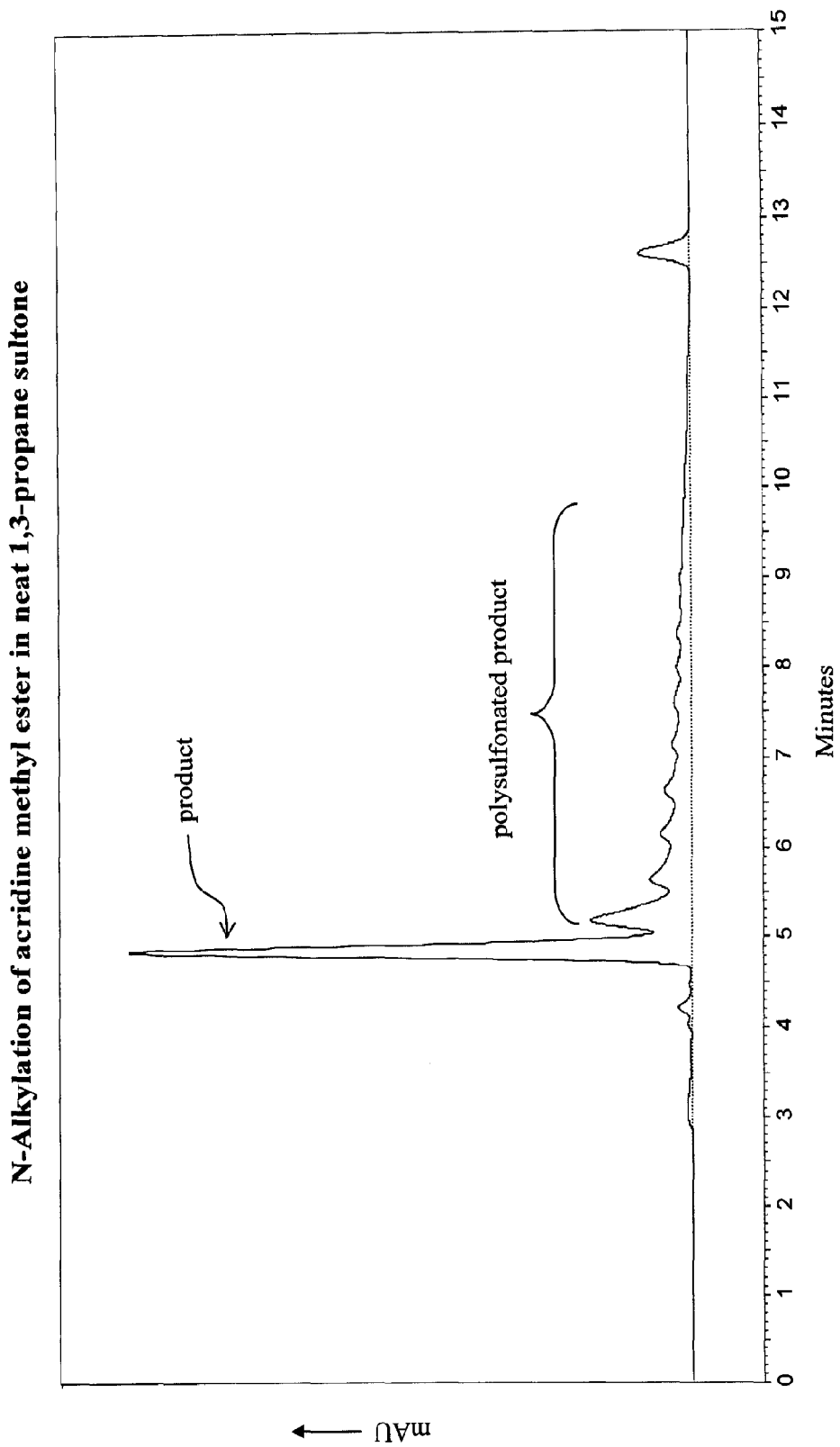
FIG. 2A is an HPLC analysis of the reaction of acridine methyl ester in neat 1,3-propane sultone showing several peaks corresponding to polysulfonate products.
Figure 2B:
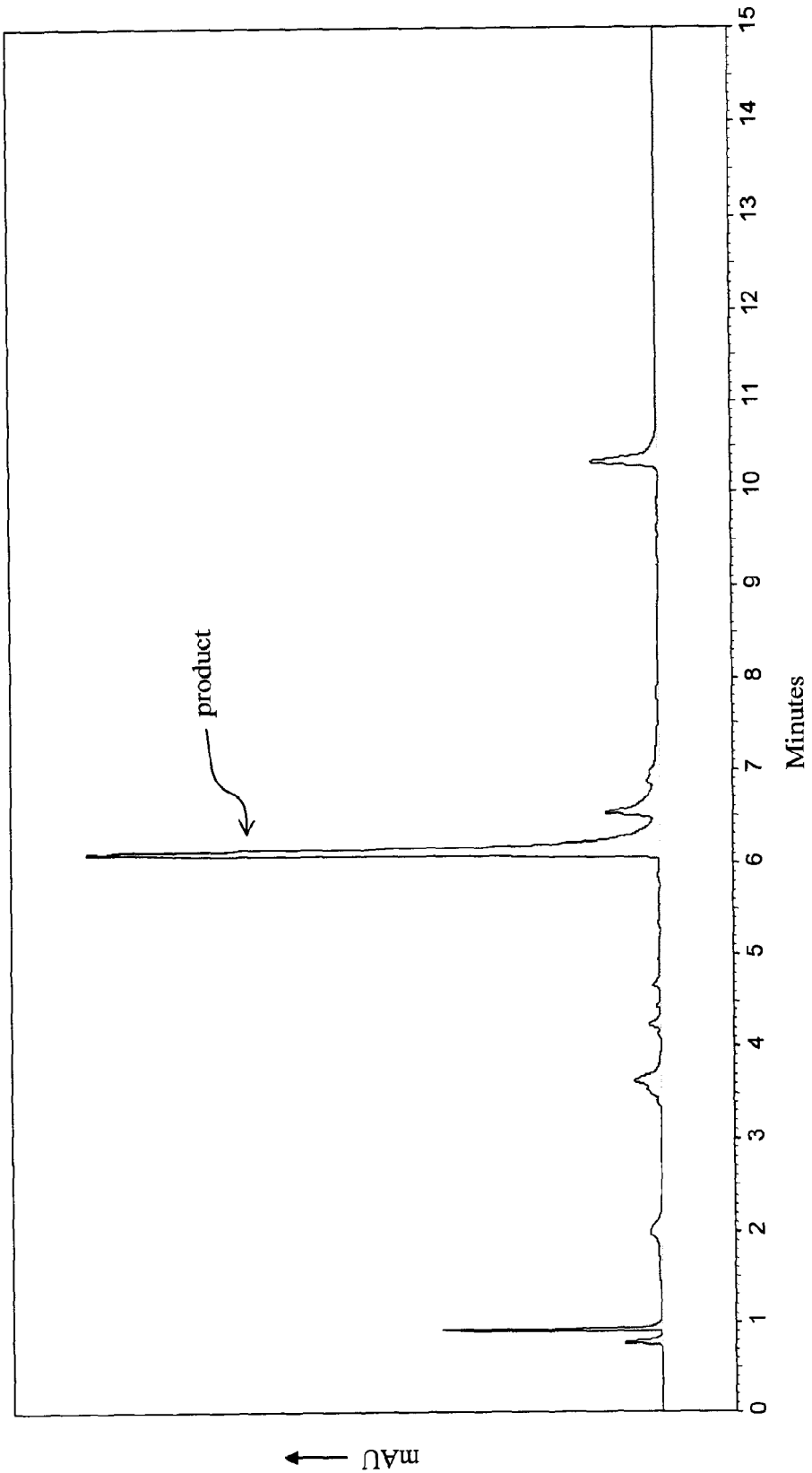
FIG. 2B is an HPLC analysis of the reaction of acridine methyl ester with 1,3-propane sultone in the ionic liquid solvent [BMIM][PF$_6$], which shows far less polysulfonate product than seen in FIG. 2A.

Surprisingly, in contrast to the other solvents, both ionic liquids proved to be excellent media for the N-alkylation of acridine methyl ester using a limited amount of propane sultone affording >80% conversion, as indicated by the results in Table 2. Although the reactions summarized in Table 2 were carried out on a small scale (25-50 mg acridine ester), scale-up of the reaction to 1-2 g of the acridine ester led to even better conversion to product (>85%). The reaction in [BMIM][PF$_6$] was carried with 2 grams of the acridine methyl ester and was conveniently worked up by diluting the reaction mixture in ethyl acetate and collecting the crude product by simple filtration. Hydrolysis of the methyl ester with hydrochloric acid followed by simple precipitation afforded a 1.68 g (66%) of the acridinium carboxylic acid and in excellent purity (94%) as described in Example 2. A similar reaction, described in Example 3, was carried out in [BMIM][BF$_4$] using 1 g of the acridine ester which, after hydrolysis of the methyl ester, led to 0.79 g of product. Both the above procedures in these two ILs required no chromatography but simple filtration to isolate the final product. In addition, the purpose of acid hydrolysis in both these procedures was mainly for hydrolysis of the methyl ester, rather than to decompose polysulfonate, as polysulfonate formation was minimal in these reactions. This is illustrated in FIGS. 2A and 2B where, HPLC analyses of the N-alkylation reactions of acridine methyl ester with propane sultone in either neat 1,3-propane sultone or in [BMIM][PF$_6$], are shown. As is evident from FIG. 2B, the reaction in ionic liquid shows mostly monosulfonated product whereas the reaction conducted in neat propane sultone (FIG. 2A) shows a significant amount of polysulfonation that is manifested as a series of peaks of diminishing intensity eluting after the main product peak.

The absence of significant polysulfonation in ionic liquids allowed for an improvement in product yield of NSP-DMAE-NHS ester as exemplified by the N-alkylation of acridine NHS ester with ten equivalents of propane sultone in [BMIM][PF$_6$]. As described in Example 4, N-alkylation of 0.5 g of the acridine precursor led to, after HPLC purification, 0.356 g (56%) of the product NSP-DMAE-NHS ester which represents a greater than doubling of the yield using five-fold less 1,3-propane sultone over the procedure described by Law et al. in U.S. Pat. No. 5,656,426, incorporated by reference herein.

In one embodiment, there will be produced at least about 50% less polysulfonation product when alkylating an acridine compound with 1,3-propane sultone in ionic liquids according to the invention as compared to the use of neat 1,3-propane sultone under otherwise identical conditions. Preferably, there will be at least about 60% less, more preferably at least about 70% less, and more preferred still at least about 80% less, and ideally at least about 90% less polysulfonation product produced with the inventive method as compared to the use of neat 1,3-propane sultone.

Figure 3:
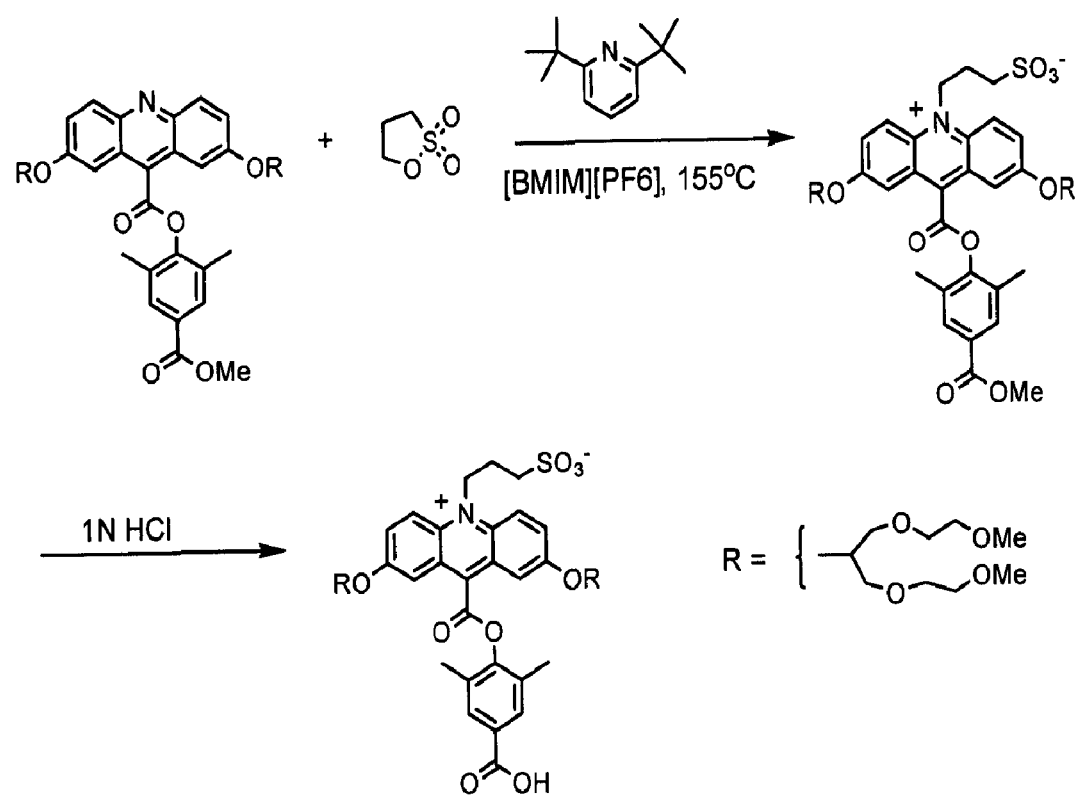
FIG. 3 illustrates the transformation of Example 5 wherein an acridine methyl ester having electron donating alkoxy (—OR) functional groups on the C2 and C7 positions of the acridine nucleus is alkylated with 1,3-propane sultone in the ionic liquid solvent [BMIM][PF$_6$] and in the presence of a sterically hindered pyridine base to provide the N-sulfopropyl (NSP) acridinium methyl ester, which is subsequently hydrolyzed in acid.

N-Alkylation with 1,3-propane sultone in ionic liquids of acridine esters containing functional groups on the acridine ring was also successfully carried out as illustrated in FIG. 3 and Example 5. In this particular example, the acridine ester has electron-donating alkoxy (OR) groups at C-2 and C-7 of the acridine ring. N-alkylation of this compound with 10 equivalents of propane sultone led to 80% conversion to product. In this case, conversion was improved by the inclusion of the base 2,6-di-t-butylpyridine in the reaction medium. Work up of the reaction after the N-alkylation reaction, followed by hydrolysis of the methyl ester and subsequent HPLC purification, led to 52% isolated yield of the final product.

The surprising discovery that N-alkylation of acridine compounds with propane sultone can be carried out in ionic liquids using a limited quantity of the sultone, yet proceed cleanly with excellent conversion and straightforward product isolation, not only offers an opportunity to curtail the use of the carcinogen propane sultone, but also offers a protocol for the scale-up synthesis of a variety of hydrophilic, acridinium compounds. In addition to [BMIM][PF$_6$] and [BMIM][BF$_4$], it is contemplated that a wide variety of ionic liquids, as described herein or otherwise generally known, will be useful in the present invention. A 5-20 fold excess of ionic liquid over the acridine compound is preferred in the N-alkylation reaction although other ratios are also likely to also be useful because the ionic liquid is simply the reaction solvent.

The reaction temperature useful for achieving the N-alkylation reaction of acridine esters will typically be between about 100° C. and about 200° C., preferably in the range of about 120° C. to about 160° C. Heating can be accomplished thermally such as in an oil-bath or by microwave heating. The reaction times most useful to achieve good chemical conversion (i.e., >70%) may span the range of about 3 to about 24 hours although about 16 to about 24 hours is preferable. Reaction times longer than 24 hours may likely be employed to further improve chemical conversion.

The alkylation reaction in ionic liquids disclosed herein is extremely versatile, due in part to the fact that polysulfonation is largely prevented, thus avoiding the need for acid hydrolysis which would otherwise interfere with acid-labile functional groups in the molecule. Thus, there is essentially no limitation on the structure of the acridine compounds which can be N-alkylated according to the invention, with the possible exception that strongly nucleophilic functional groups which may react with the alkylating agent should be avoided or should be protected with a suitable protecting group prior the carrying out the N-alkylation reaction. In one embodiment, the starting acridine compounds used in the present invention are acridine esters having the following structure:

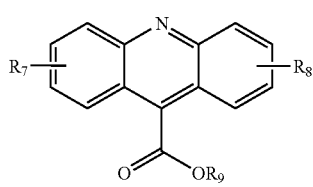

(Va)

where $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms; and $R_9$ is a substituted or unsubstituted alkyl or aryl moiety, typically a substituted aryl moiety having functional groups for forming conjugates with analytes, analyte analogs, or antibodies for such analytes. In one embodiment, $R_7$ and $R_8$ each represent hydrogen. In another embodiment, $R_7$ and $R_8$ are substituents on the C2 and C7 carbon atoms of the acridine nucleus, respectively. In a particularly interesting variant of the case where $R_7$ and $R_8$ are of the form —OR, R may comprise one or more ethylene glycol units of the form —(O—CH$_2$—CH$_2$)$_n$— (n=1-5) or may comprise sulfonylpropyl groups (—CH$_2$—CH$_2$—CH$_2$—SO$_3^-$), or combinations thereof, such as for example —(O—CH$_2$—CH$_2$)$_n$—CH$_2$—CH$_2$—CH$_2$—SO$_3^-$ or —CH$_2$—CH$_2$—CH$_2$—SO$_2$—NH—(O—CH$_2$—CH$_2$)$_n$—, or the like, and R may optionally be a branched substituent, as illustrated in FIG. 3.

Preferred structures of the acridine esters according to this embodiment will have the structure:

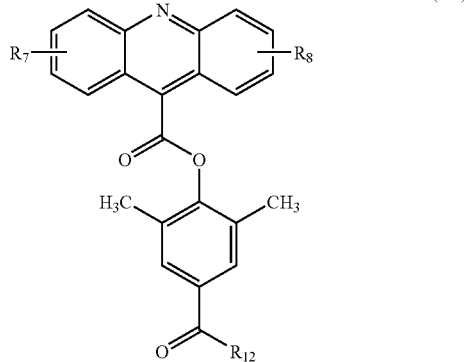

(Vb)

where $R_7$ and $R_8$ are as defined above, and $R_{12}$ is selected from the group consisting of:
(i) —OR (where R is as defined above);
(ii) —O—N-succinimidyl;
(iii) —NH—(CH$_2$)$_5$—C(=O)—O—N-succinimidyl; and
(iv) —NH—(C$_2$H$_4$O)$_n$—C$_2$H$_4$NH—C(=O)—(CH$_2$)$_3$—C(=O)—O—N-succinimidyl, wherein n=0 to 5.

Other preferred structures of the acridine ester compounds have the form:

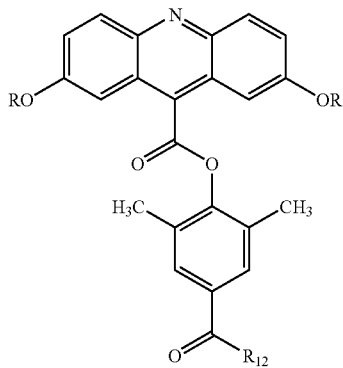

Vc where $R_{12}$ is as defined above; and R is independent selected at each occurrence and is as also defined above.

In another embodiment, acridine sulfonamide compounds may be used as the starting acridine compound in the transformation to acridinium sulfonamides. Typically, the acridine sulfonamides will have the following structure:

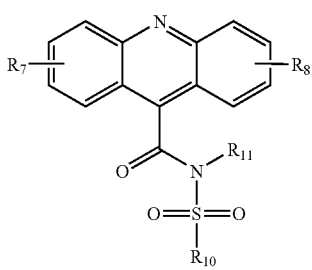

(VIa)

where $R_7$ and $R_8$ are independently selected and are as defined above, and $R_{10}$ and $R_{11}$ can be the same or different and represent an alkyl, alkenyl, alkynyl, aryl, or aralkyl group containing up to 20 heteroatoms.

To optimize the yield in the N-alkylation of acridine compounds containing electron-donating groups (e.g., —OR) on the acridine nucleus, it is preferred to include a base in the reaction mixture, preferably a pyridine derivative, and more preferably a sterically hindered pyridine derivative which will not react with the alkylating reagent. The preferred bases are 2,6-di-t-butylpyridine or 2,6-di-t-butyl-4-methylpyridine in the preferred molar ratio of 1:2 (base:alkylating reagent), although other ratios are also likely to be useful.

Further examples of compounds which can be prepared according to the methods of the invention include all acridinium esters and acridinium sulfonamides disclosed in U.S. Patent Pub. 2005/0221390 and U.S. Patent Pub. 2004/0063147, the disclosures of which are hereby incorporated by reference herein.

EXAMPLE 1

General Procedure for the Small Scale N-Alkylation of 2',6'-dimethyl-4'-methoxycarbonylphenyl acridine-9-carboxylate with Propane Sultone in Various Solvents The following procedure illustrated in DMF solvent was typical. A mixture of 2',6'-dimethyl-4'-methoxycarbonylphenyl acridine-9-carboxylate (50 mg, 0.13 mmol) and distilled 1,3-propane sultone (160 mg, 10 equivalents) in anhydrous DMF (0.5 mL) was heated in an oil bath at 155-160° C. After 6 hours, HPLC analysis was performed using a 4.6×30 cm, C18 column and a 30-minute gradient of 10%→100% MeCN/water (each with 0.05% TFA) at a flow rate of 1 mL/min and UV detection at 260 nm indicated product eluting at ~17.5 minutes. Comparison with the amount of unreacted starting material eluting at 26 minutes indicated approximately 40% conversion.

Small-scale reactions in other solvents were performed similarly.

EXAMPLE 2

N-Alkyation on a Gram Scale of 2',6'-dimethyl-4'-methoxycarbonylphenyl acridine-9-carboxylate with Propane Sultone in [BMIM][PF6]

Synthesis of 2',6'-dimethyl-4'-carboxyphenyl-10-sulfopropylacridinium-9-carboxylate To an 8 dram vial was added 2.0 g (5.19 mmol) of the acridine ester, 15 g (52.8 mmol) of 1-butyl-3-methylimidazolium hexafluorophosphate (Fluka) and 6.34 g (51.9 mmol) of distilled 1,3-propane sultone under nitrogen. This sealed vial was heated to 155° C. for 24 hours. Then the reaction mixture was cooled to 40° C. and added drop wise into 500 ml of ethyl acetate with stirring which gave a yellow precipitate. The mixture was stirred at room temperature for 2 hours and filtered. The filter cake was washed with ethyl acetate (50 ml×3) and dried under high vacuum which gave 6.19 g of a yellow solid which was then treated as follows.

The above 6.19 g of crude acridinium ester was added to 80 ml of HCl solution (8 ml concentrated HCl and 72 ml de-ionized water). The reaction mixture was heated to 110° C. for 4 hours and then cooled to 2-8° C. overnight. A yellow precipitate was formed which was filtered. The filter cake was washed with de-ionized water (40 ml×3) and diethyl ether (20 ml×2) and dried under high vacuum over $P_2O_5$ which gave 1.68 g yellow powder (66% yield from 2',6'-dimethyl-4'-methoxycarbonylphenyl acridine-9-carboxylate, 94% purity by HPLC).

EXAMPLE 3

N-Alkyation on a Gram Scale of 2',6-dimethyl-4'-methoxycarbonylphenyl acridine-9-carboxylate with Propane Sultone in [BMIM][BF4]

Synthesis of 2',6'-dimethyl-4'-carboxyphenyl-10-sulfopropylacridinium-9-carboxylate To an 8 dram vial was added 1.0 g (2.6 mmol) of the acridine ester, 10 g (44.2 mmol) of 1-butyl-3-methylimidazolium tetrafluoroborate [BMIM][BF$_4$] (Fluka) and 3.18 g (26.0 mmol) of distilled 1,3-propane sultone under nitrogen. This sealed vial was heated to 155° C. for 24 hours. Then the reaction mixture was cooled to room temperature which gave a red, clear liquid (83% conversion to product by HPLC). The above red clear liquid of the acridinium methyl ester was added to a 30 ml of 1 M HCl solution. The reaction mixture was heated to 110° C. for 4 hours and then cooled to room temperature which gave a red solution. The reaction mixture was poured into a 1000 ml of de-ionized water and a yellow precipitate was formed. The mixture was kept in the refrigerator overnight. The yellow precipitate was then filtered and washed with de-ionized water (40 ml×3) and diethyl ether (40 ml×3). It was then dried under high vacuum over $P_2O_5$ which gave 0.793 g of product as a yellow powder (62% yield from acridine ester, 81% purity by HPLC).

EXAMPLE 4

N-Alkyation on a Half-Gram Scale of 2',6-dimethyl-4'-N-succinimidyloxycarbonylphenyl acridine-9-carboxylate with Propane Sultone in [BMIM][PF6]

Synthesis of 2',6'-dimethyl-4'-N-succinimidyloxycarbonylphenyl-10-sulfopropylacridinium-9-carboxylate (NSP-DMAE-NHS)

To an 8 dram vial was added 0.50 g (1.07 mmol) of 2',6-dimethyl-4'-N-succinimidyloxycarbonylphenyl acridine-9-carboxylate, 5 g (17.6 mmol) of 1-butyl-3-methylimidazolium hexafluorophosphate [BMIM][PF$_6$] (Fluka) and 1.31 g (10.7 mmol) of distilled 1,3-propanesultone under nitrogen. This sealed vial was heated to 155° C. for 16 hours. Then the reaction mixture was cooled to 40° C. and added drop wise to 100 ml of ethyl acetate with stirring which gave a yellow precipitate. The mixture was stirred at room temperature for 2 hours and filtered. The filter cake was washed with ethyl acetate (30 ml×2) and dried under high vacuum which gave 0.753 of a yellow solid. The crude product was purified by preparative HPLC on Waters system using an YMC, C18 column, 50×500 mm, with a solvent flow rate of 60 ml/minute, UV detection at 260 nm, elution being performed with 35% B over 50 minutes (A: water/0.05% TFA; B: acetonitrile/0.05% TFA). After lyophilization of the HPLC fractions, the desired product NSP-DMAE-NHS ester, 0.356 g (56% yield), was obtained as a yellow powder.

EXAMPLE 5

N-Alkylation of an Acridine Ester Containing Electron-Donating Groups in the Acridine Ring with Propane Sultone in [BMIM][PF6]

The acridine ester illustrated in FIG. 3 (78 mg, 98 umoles), distilled 1,3-propane sultone (120 mg, 10 equivalents) and 2,6-di-t-butylpyridine (0.110 mL, 5 equivalents) were combined in 1.2 g [BMIM][PF$_6$] and heated at 155° C. in an oil bath for 24 hours. The reaction was then cooled to room temperature and analyzed by HPLC as described in example 1. Approximately 80% conversion to product eluting at 19 minutes was observed with starting material eluting at 25 minutes. The crude reaction mixture was dissolved in ethyl acetate (5 mL) and applied to a silica column. The column was first eluted with ethyl acetate (500 mL) followed by 1:1 ethyl acetate/methanol. The fractions containing product were combined and concentrated under reduced pressure which afforded 165 mg of a sticky solid. This product was suspended in 10 mL of 1N HCl and refluxed under nitrogen. After 1 hour, HPLC analysis indicated complete hydrolysis of the methyl ester and showed product eluting at 16.4 minutes. The product was purified by preparative HPLC using an YMC C18, 30×300 mm column. The HPLC fractions were concentrated under reduced pressure. Yield=46 mg (52% overall).

The patents, patent documents, and publications cited herein are incorporated by reference in their entirety, as if each were individually incorporated by reference. Various modifications and alterations of this invention will become apparent to those skilled in the art without departing from the scope and spirit of the invention encompassed by the appended claims.

We claim:

1. A method for N-alkylation of an acridine compound, the method comprising providing a reaction mixture comprising said acridine compound, an alkylating agent, and an ionic liquid solvent, and heating said reaction mixture to between about 100° C. and about 200° C., to thereby convert said acridine compound to an N-alkyl acridinium compound.

2. The method according to claim 1, wherein said ionic liquid solvent is of the form:

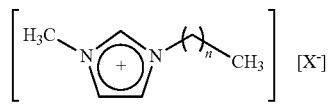

where n is an integer from one to nine; and

X is selected from the group consisting of tetrachloroaluminate; hexafluroantimonate; dicyanamide; thiocyanate; nitrate; chloride; iodide; trifluoroacetate; tetrafluoroborate; hexafluorophosphate; methylsulfonate; trifluoromethylsulfonate; tris(pentafluoroethyl)trifluorophosphate; bis(trifluoromethylsulfonyl)imide; and combinations thereof.

3. The method of claim 2, wherein X is tetrafluoroborate or hexafluorophosphate.

4. The method according to claim 3, wherein n is 3.

5. The method according to claim 4, wherein the ionic solvent comprises [BMIM][PF$_6$] (1-butyl-3-methylimidazolium hexafluorophosphate).

6. The method according to claim 4, wherein the ionic solvent comprises [BMIM][BF$_4$] (1-butyl-3-methylimidazolium tetrafluoroborate).

7. The method according to claim 1, wherein said alkylating agent is selected from the group consisting of: sultones; esters of haloacetic acid; alkyl halides; and alkyl triflates; wherein said alkyl groups optionally comprise one or more heteroatoms and optionally include one or more unsaturated bonds.

8. The method according to claim 7, wherein said alkylating agent is a sultone.

9. The method according to claim 8, wherein said sultone has the structure:

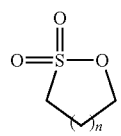

where n=1 or 2.

10. The method according to claim 9, wherein said sultone is 1,3-propane sultone.

11. The method according to claim 1, wherein said acridine compound is an acridine ester.

12. The method according to claim 1, wherein said acridine compound is an acridine sulfonamide.

13. The method according to claim 1, wherein said reaction mixture further comprises a base which is unreactive with said alkylating agent under the reaction conditions.

14. The method according to claim 13, wherein said base is a sterically hindered pyridine derivative.

15. The method according to claim 14, wherein said base comprises 2,6-di-t-butylpyridine (DtBP) or 2,6-di-t-butyl-4-methylpyridine (DtBMP), or a combination thereof.

16. The method according to claim 1, the molar ratio of said alkylating agent to said acridine compound is less than about 20:1, said ionic liquid solvent is present in a molar ratio to said acridine compound of at least about 1:1, and wherein said reaction mixture is heated for about 3 to about 24 hours at a temperature between about 120° C. and about 160° C.

17. The method accordingly to claim 1, wherein the percent chemical conversion to said N-alkyl acridinium derivative is at least about 70%.

18. The method according to claim 1, wherein the percent chemical conversion to said N-alkyl acridinium derivative is at least about 80%.

19. A method for preparing an acridinium ester compound having the structure of formula (V):

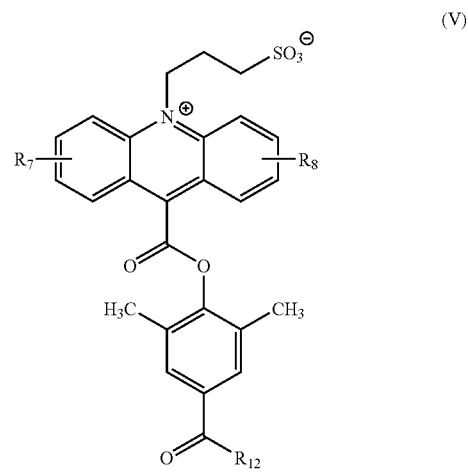

wherein R$_7$ and R$_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; and wherein R$_{12}$ is selected from the group consisting of:

(i) —OR;

(ii) —O—N-succinimidyl;

(iii) —NH—(CH$_2$)$_5$—C(=O)—O—N-succinimidyl; and (iv) —NH—(C$_2$H$_4$O)$_n$—C$_2$H$_4$NH—C(=O)—(CH$_2$)$_3$—C(=)—O—N-succinimidyl, wherein n=0 to 5;

the method comprising:

(1) providing a reaction mixture comprising an acridine compound, 1,3-propane sultone, and an ionic liquid solvent, the acridine compound having the structure of formula (Vb):

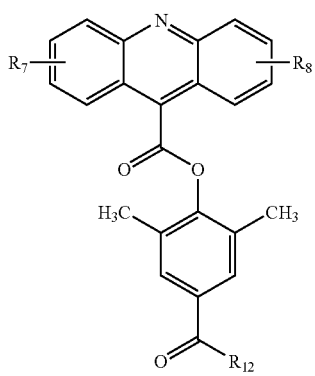

(Vb)

wherein $R_7$, $R_8$, and $R_{12}$ are as defined above; and (2) heating said reaction mixture to between about 100° C. and about 200° C., to thereby convert said acridine compound of formula (Vb) to said acridinium ester compound of formula (V).

20. A method for preparing an acridinium sulfonamide compound having the structure of formula (VI):

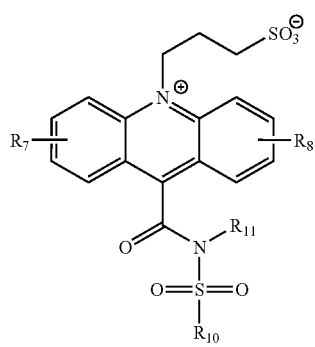

(VI)

wherein $R_7$ and $R_8$ can be the same or different, and are selected from the group consisting of hydrogen, halogen, —OR, and R; where R is an alkyl, alkenyl, alkynyl, aryl, or aralkyl group containing up to 20 heteroatoms selected from oxygen, sulfur, and nitrogen; and wherein $R_{10}$ and $R_{11}$ can be the same or different and represent alkyl, alkenyl, alkynyl, aryl, or aralkyl groups containing up to 20 heteroatoms;

the method comprising:

(1) providing a reaction mixture comprising an acridine compound, 1,3-propane sultone, and an ionic liquid solvent, the acridine compound having the structure of formula (VIa):

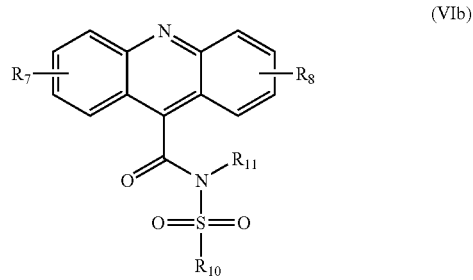

(VIb)

wherein $R_7$, $R_8$, $R_{10}$ and $R_{11}$ are as defined above; and (2) heating said reaction mixture to between about 100° C. and about 200° C., to thereby convert said acridine compound of formula (VIb) to said acridinium sulfonamide compound of formula (VI).

\* \* \* \* \*